United States Patent [19]
Van Agthoven et al.

[11] Patent Number: 6,143,567
[45] Date of Patent: Nov. 7, 2000

[54] REAGENTS AND A METHOD FOR THE LYSIS OF ERYTHROCYTES

[75] Inventors: André Van Agthoven; David Jarrossay, both of Marseilles, France

[73] Assignee: Immunotech, Marseille Cedex, France

[21] Appl. No.: 09/305,361

[22] Filed: May 5, 1999

[30] Foreign Application Priority Data

May 7, 1998 [FR] France .................................. 98 06055

[51] Int. Cl.[7] .................................................. G01N 31/00
[52] U.S. Cl. .................................... 436/10; 436/8; 436/10; 436/17; 436/18; 436/63; 252/408.1
[58] Field of Search .................... 436/8, 10, 17, 436/18, 63, 166, 175; 252/408.1

[56] References Cited

U.S. PATENT DOCUMENTS

| | | | |
|---|---|---|---|
| 3,884,579 | 5/1975 | Mauthner | 356/39 |
| 4,284,412 | 8/1981 | Hansen et al. | 435/7.24 |
| 4,637,986 | 1/1987 | Brown et al. | 436/10 |
| 4,902,613 | 2/1990 | Chang et al. | 435/2 |
| 5,188,935 | 2/1993 | Leif et al. | 435/7.24 |
| 5,316,951 | 5/1994 | Carver, Jr. et al. | 436/63 |
| 5,599,682 | 2/1997 | Van Agthoven | 435/7.24 |
| 5,627,213 | 5/1997 | Van Agthoven | 514/557 |
| 5,968,832 | 10/1999 | Uchihashi et al. | 436/10 |

*Primary Examiner*—Maureen M. Wallenhorst
*Attorney, Agent, or Firm*—Browdy and Neimark

[57] ABSTRACT

The lysis of erythrocytes is accomplished by subjecting whole blood treated with an anticoagulant at a pH between 4 and 9 with a nitrogenous heterocyclic compound, most preferably pyrrolidine chloride.

26 Claims, 5 Drawing Sheets

REAGENTS AND A METHOD FOR THE LYSIS OF ERYTHROCYTES

The present invention relates to a new reagent and a method for the lysis of erythrocytes which is non-toxic for leucocytes and compatible with the use of a fixing agent of the aliphatic aldehyde type.

BACKGROUND OF THE INVENTION

In a normal blood, erythrocytes are about one thousand times more abundant than leucocytes and form an obstacle to any study or analysis of leucocytes. This is why methods of leucocyte analysis such as cytometry, or cytospin involving centrifugation of the blood constituents, are preceded in most cases by a step for separating erythrocytes from leucocytes (U.S. Pat. No. 4,284,412, EPA-0 022 670).

One such separation by centrifugation using Ficoll to isolate the lymphocytes and granulocytes from the blood has been described by Boyem in Scandinavian Journal of Clinical and Laboratory Investigation 1967–68, Suppl. 94–101.305.293 and Pertoff in Journal of Immunological Methods: 1980, 33:221–229.

These methods are relatively difficult to use because they require several washes and centrifugations, which may lead to losses of cells and hence to an assay by default. However, said methods are currently considered to be reference methods since the morphology and viability of the leucocytes are preserved after separation.

The lysis of blood with a view to a leucocyte analysis involves the destruction of the red corpuscles to a state of debris. The lysis methods, on the other hand, aim for optimum preservation of the morphology of the leucocytes in order to permit a cytometric leucocyte analysis and to distinguish the leucocytes clearly from the erythrocyte debris.

The lysis of erythrocytes is based on the general principle of passing a quantity of material through the membrane from the outside of the erythrocyte. During this passage, the condition of the membrane deteriorates either due to swelling of the cell or due to dissolution of the membrane in the material passing through.

The preservation of the leucocyte morphology during lysis is based on a more protein-rich environment around its membrane: outside and inside, transmembrane proteins, and inside, a developed cytoskeleton.

The advantage of this leucocyte membrane support is exploited to the full by the use of fixing agents such as formaldehyde which penetrates the membrane and fixes the protein structures by crosslinking outside and inside.

The material used for passing through the erythrocyte membranes are generally small neutral molecules, firstly water itself, used in hypotonic lysis, or water in the presence of diethylene glycol, formaldehyde and citric acid as in Chang et al. (U.S. Pat. No. 4,902,613). Sometimes, fixing and hypotonic lysis are carried out at different stages as described by Quintana (WO-89/0509) and van Agthoven (EPA-0625706).

In the case of isotonic lyses as described in EP-A-625 707, the material passed through is composed of a mixture of formaldehyde, glycerol, butanol and citric acid.

Another method of isotonic lysis uses saponin, a small molecule with detergent properties as described in WO 85/05640.

There is a method of lysis wherein the general principle of lysis is not immediately apparent. This is lysis with ammonium chloride. The lysis operation depends on the passage of $NH_3$ and $CO_2$ through the membrane. $NH_3$ and $CO_2$ are in equilibrium with $NH_4^+$ and $HCO_3^-$ in the mixture. The spontaneous re-conversion of $NH_3$ to $NH_4^+$ in the cell and of $CO_2$ to $HCO_3^-$ by carbonic anhydrase present in large quantities in the erythrocyte could be the force behind a continuous flow of $NH_3$ and $CO_2$ entering the cell.

Lysis with ammonium chloride is the most effective lysis that can be carried out in the absence of fixing agent and it is therefore the preferred method of many research laboratories. A limitation of this method is that the leucocytes very quickly lose their viability during the lysis process. Apparently, the interior of the cell is initially rendered alkaline by the product of the two reactions; $NH_5CO_3$. Later on, in the reaction after lysis and release of carbonic anhydrase from the erythrocytes, the reaction $HCO_3 \rightarrow CO_2 + OH^-$ from the bicarbonate present in the lysis buffer renders the entire mixture alkaline, which brings about the degradation of the leucocytes. Due to these toxic conditions, the reading must be taken very rapidly, usually 1 to 2 hours after carrying out the preparation.

Another limitation of the method is the fact that it is impossible to combine the use of ammonium chloride with formaldehyde due to the following reaction:

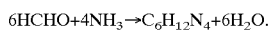

$$6HCHO + 4NH_3 \rightarrow C_6H_{12}N_4 + 6H_2O.$$

The hexamethylene tetramine formed is stable and consequently the mixture acidifies during the reaction to the detriment of the leucocytes because the removal of $NH_3$ in the medium shifts the equilibrium and the $H^+0$ ions are no longer compensated for.

To summarise, ammonium chloride has proved to be incompatible with aliphatic aldehydes and consequently lysis stops rapidly when both are used together.

SUMMARY OF THE INVENTION

It would be advisable, therefore, to have a lysis reagent and a method for the lysis of erythrocytes which retain as far as possible the cell viability of the leucocytes. It would also be desirable to have a lysis reagent and a method for the lysis of erythrocytes which allow the cytometric reading to be carried out a long time after carrying out the preparation, for example, one or more days after the reaction of the products.

It would also be desirable to have a lysis reagent and a method for the lysis of erythrocytes which are compatible with the use of formaldehyde.

After lengthy research, the applicant discovered that the above problems were solved by using a nitrogenous heterocyclic compound as lysis agent.

For this reason, the present application provides a lysis reagent which can be used for the cytometric analysis of leucocytes, characterised in that the lysis agent is a nitrogenous heterocyclic compound used at a pH between 4 and 9, preferably between 5 and 8, particularly between 6 and 7.5, more particularly between 6.8 and 7.2.

The term "lysis agent" means that the nitrogenous heterocyclic compound is the principal lysis agent used.

The applicant discovered, in fact, that the use of a nitrogenous heterocyclic compound as a lysis agent gave results which are comparable with $NH_4Cl$ whilst being compatible with the use of formaldehyde to protect the leucocytes. It would appear that the aliphatic aldehydes react with the nitrogenous heterocyclic compounds, but the reaction in the lysis medium is not complete and the products generally remain in equilibrium without forming a stable reaction product.

The nitrogenous heterocyclic compound may be bicyclic, for example, and preferably monocyclic. It may be unsaturated, in which case it contains for example 5 and preferably 4, notably 3, particularly 2 double bonds, and it is preferably saturated. It contains, for example, 3 to 8, notably 3 to 6 and particularly 3 to 5 and more particularly 4 or 5 carbon atoms. It has 2, notably 1 single nitrogen atom.

Examples of saturated nitrogenous heterocyclic compounds include pyrazolidine, imidazolidine and imidazoline, piperazine, notably morpholine and particularly piperidine or pyrrolidine.

In a lysis reagent according to the invention, the nitrogenous heterocyclic compound may be present in the molar concentration of 0.01 to 0.2M, particularly 0.05 to 0.19M and more particularly 0.1 to 0.18M. Under entirely preferential conditions of use of the lysis reagent described above, a concentration of 0.15M is used.

The concentrations are given in relation to the quantity of compound concerned in the medium during erythrocyte lysis.

Under other preferential conditions of use of the invention, the compound used according to the invention to confer the desired pH on the lysis reagent described above uses chlorine as the anion, for example, in the form of HCl. This compound is preferably an acid.

Under yet other preferential conditions of use, the lysis reagent of the invention also contains, apart from the anion used according to the invention to confer the desired pH on the lysis reagent described above, a counter-ion which is a carbonate, hydrogen carbonate or but preferably a borate. These ions may be supplied in the form of an acid but preferably in the form of a salt, for example, of sodium, particularly of potassium.

In fact, it has been found that borate was not subject to degradation like bicarbonate, and therefore contributes to the good stabilisation of the cells, allowing a cytometric reading long after lysis has been carried out. Moreover, its use allows the preparation of a stable lysis solution, which is not the case with hydrogen carbonate.

In a lysis reagent according to the invention, the counter-ion may be present in the molar concentration of 0.001 to 0.2M, particularly 0.005 to 0.1M and more particularly 0.01 to 0.05M. According to the invention, the borate is used in higher concentrations than the carbonate. For example, a concentration of 0.04M borate is used for a concentration of 0.01M carbonate or hydrogen carbonate.

Under other preferential conditions of use of the invention, the lysis reagent of the invention also contains an effective quantity of a buffer agent particularly pH 6.5 to 7.5. Examples of buffer agents include MES (2-(N-morpholino) ethane sulfonic acid), notably MOPS (3-(N-morpholino) propane sulfonic acid) and particularly HEPES (N-(2-hydroxyethyl)piperazine-N'-(2-ethane sulfonic acid)).

In a lysis reagent according to the invention, the buffer agent may be present in the molar concentration of 0.0001 to 0.05M, particularly 0.0005 to 0.03M and more particularly 0.002 to 0.008M.

Under yet other preferential conditions of use of the invention, the lysis reagent of the invention also contains an effective quantity of an anticoagulant.

Examples of anticoagulants include heparin, notably the citrate ion, and particularly EDTA.

Under entirely preferential conditions of use of the invention, a mixture of 0.15M pyrrolidine chloride, 0.04M boric acid, 0.0001 M EDTA and 0.005M HEPES is used at a pH of around 7.0.

Under yet other preferential conditions of use of the lysis reagent described above, a fixing agent is used in addition, notably an aliphatic aldehyde such as one containing $C_1$–$C_5$, for example paraformaldehyde and particularly formaldehyde.

The aliphatic aldehyde may be present in a concentration of 0.01% to 5%, particularly 0.14% to 1% and more particularly 0.1% to 0.5%. Under preferential conditions of use of the lysis reagent described above with fixing agent, 0.15M pyrrolidine chloride, 0.04M boric acid, 0.0001M EDTA, 0.005M HEPES and 0.3% of formaldehyde is used.

The present invention also provides a method for the lysis of erythrocytes wherein a sample of whole blood treated with an anticoagulant such as EDTA, heparin or citrate ions is subjected to the action of a lysis reagent described above.

It is possible to operate in the absence or in the presence of monoclonal antibodies in order to label the leucocyte cells. These antibodies may or may not be bound to a fluorescent compound such as those described below. Under preferential conditions of use, these antibodies are bound to a fluorescent compound.

The lysis reagents described above may be used as follows:

A sample of 0.1 ml of blood treated with an anticoagulant and incubated beforehand with a monoclonal antibody or a monoclonal antibody combined with a fluorescent marker or a mixture of monoclonal antibodies combined with fluorescent markers is brought into contact with 2 ml of above-mentioned lysis reagent preheated to a temperature of 37° C. and left to cool for ten minutes during which time lysis is completed. Such markers are, for example, CD45-FITC (CD45 combined with fluorescein isothiocyanate) or CD14 combined with phycoerythrin and are sold, for example, by the companies DAKO, BECTON and DICKINSON or IMMUNOTECH. The reading is then carried out in a cytometer, for example, of the BECTON and DICKINSON Facscan type, either immediately or up to 3 days after lysis.

Under preferential conditions of use according to the invention, the preferential conditions described above are chosen for the lysis reagent and lysis method.

Figure 1A:
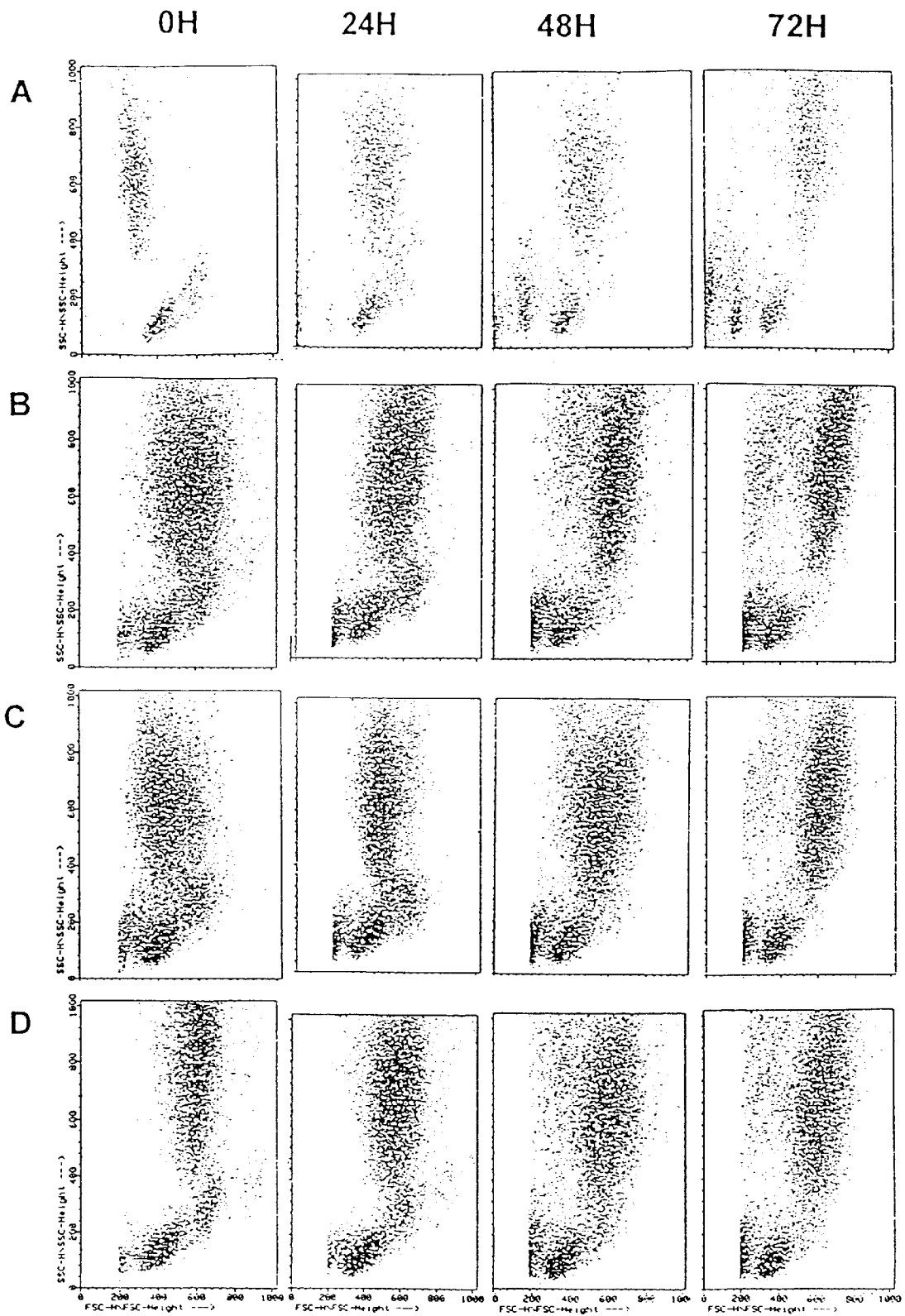
FIGS. 1a to 1d represent the results obtained by cytometry using a Facscan from BECTON and DICKINSON by comparing the diffusion at large and small angles: immediately after (0 h) and 24 h, 48 h and 72 h after lysis.
Figure 1:
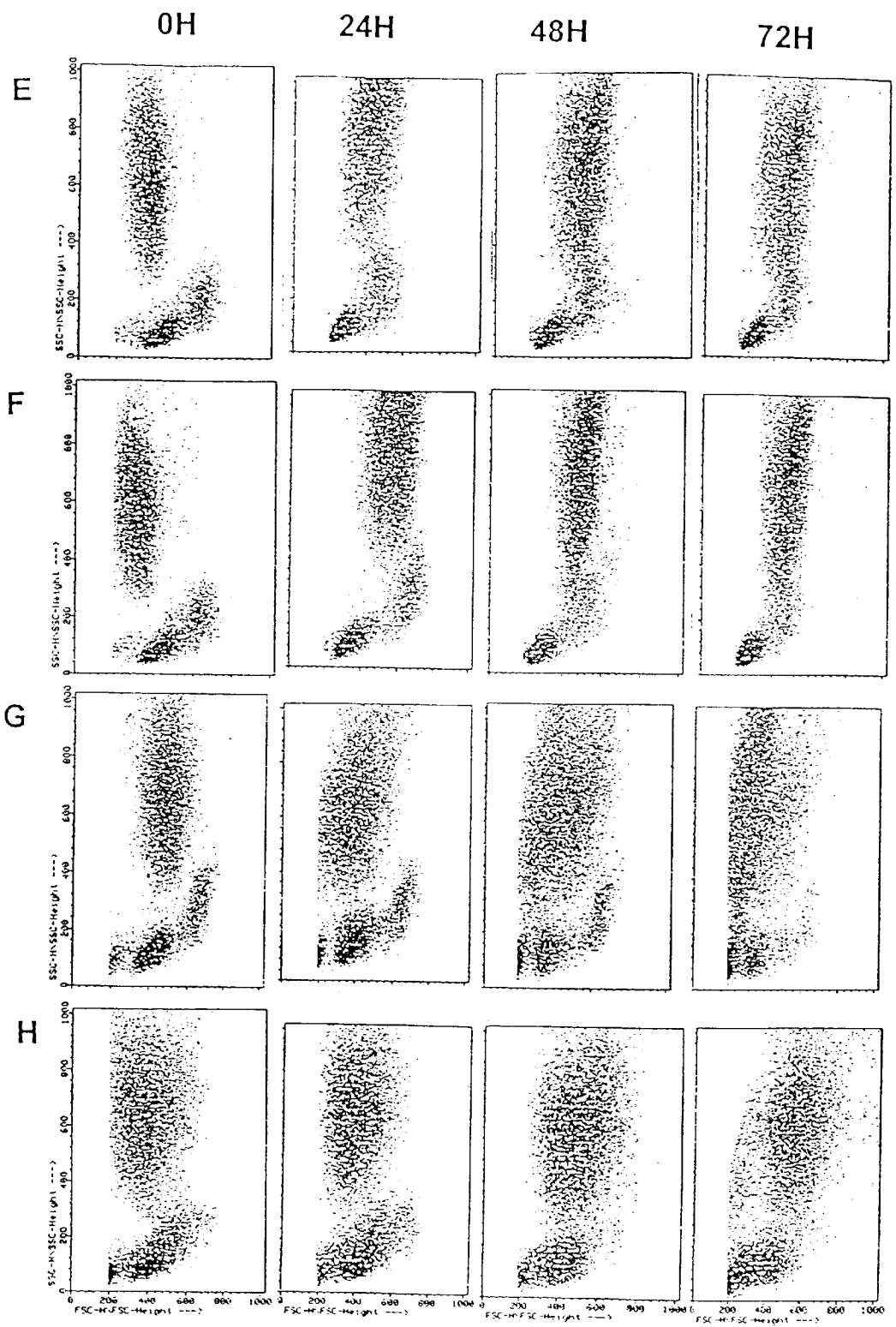
Figure 1:
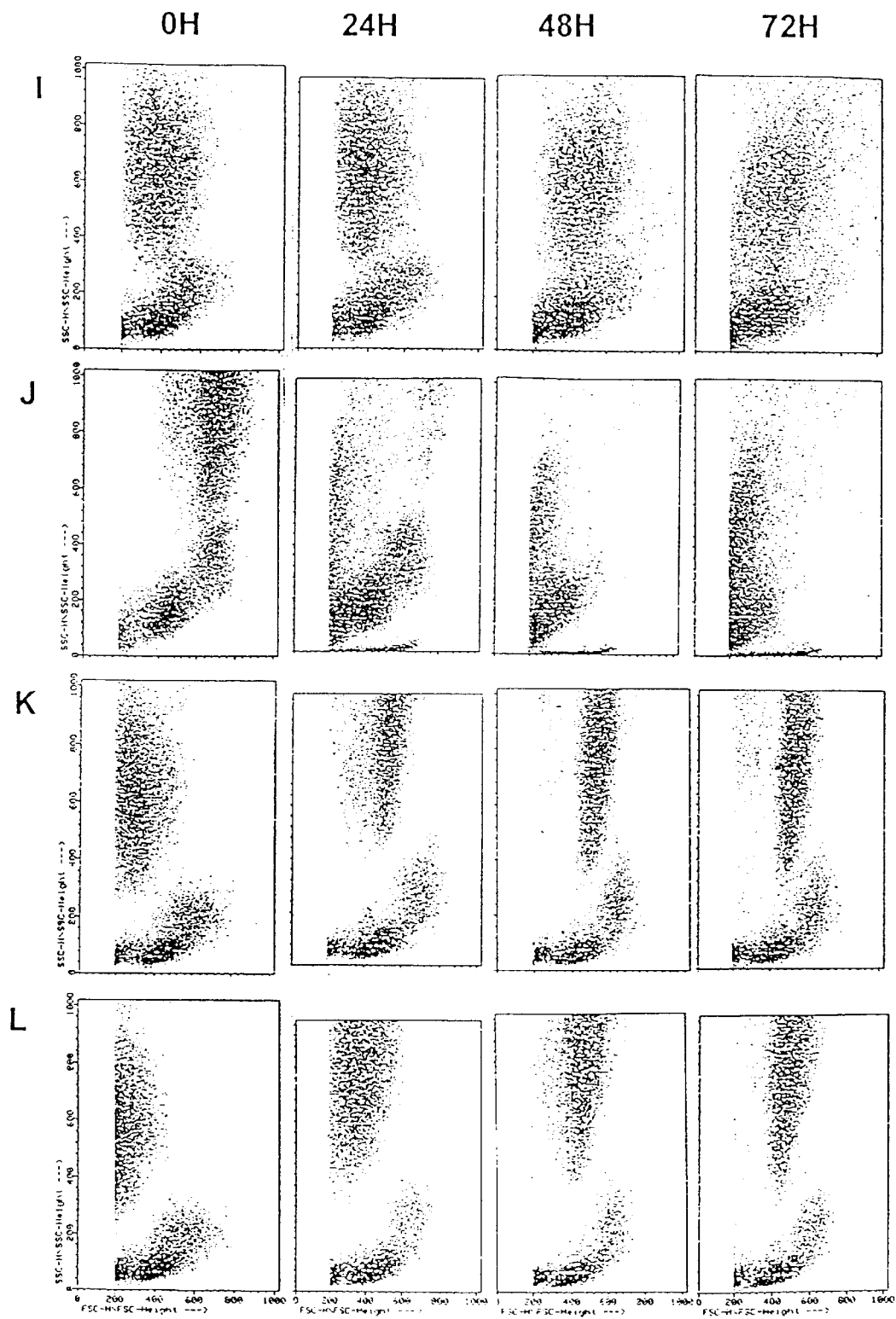
Figure 1:
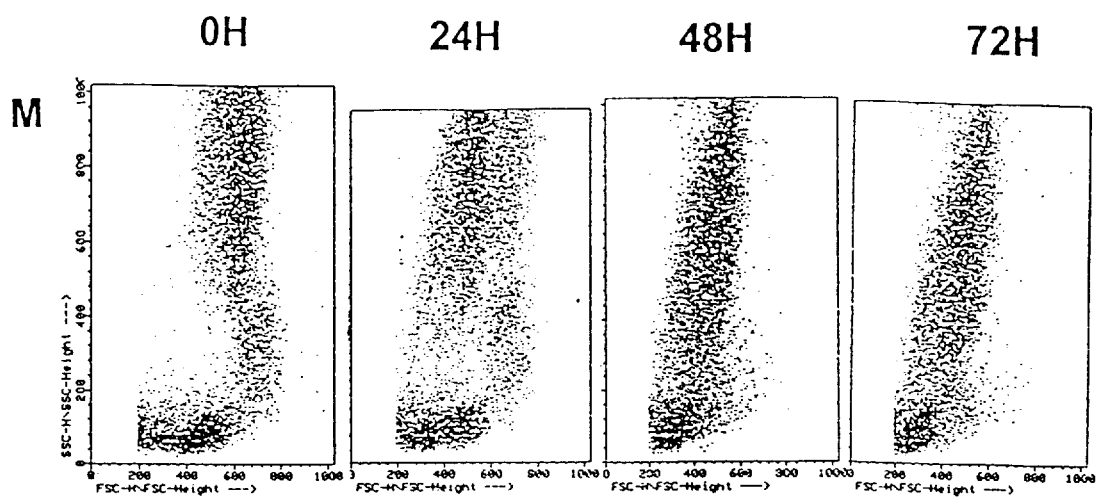

More specifically,

FIG. 1a, line A represents the results obtained for the control—no lysis reagent, FIG. 1a, line B represents the results obtained for the reagent of example 1 by carrying out washing with the phosphate buffer (PBS) 10 min after lysis, FIG. 1a, line C represents the results obtained for the reagent of example 3 by carrying out washing 10 min after lysis, FIG. 1a, line D represents the results obtained for the ORTHO DIAGNOSTIC SYSTEMS INC. reagent, reference 770521—lysis agent=$NH_4Cl$, by FIG. 1b, line E represents the results obtained for the reagent of example 2, FIG. 1b, line F represents the results obtained for the reagent of example 4, FIG. 1b, line G represents the results obtained for the ORTHO DIAGNOSTICS reagent to which 0.3% of HCHO were added, FIG. 1b, line H represents the results obtained for the reagent of example 1, but without washing, FIG. 1c, line I represents the results obtained for the reagent of example 3, but without washing, FIG. 1c, line J represents the results obtained for the ORTHO DIAGNOSTICS reagent, but without washing, FIG. 1c, line K represents the results obtained for the reagent of example 2, but without washing, FIG. 1c, line L represents the results obtained for the reagent of example 4, but without washing, FIG. 1d, line M represents the results obtained for the ORTHO DIAGNOSTICS reagent to which 0.3% of HCHO were added, but without washing.

Figure 2:
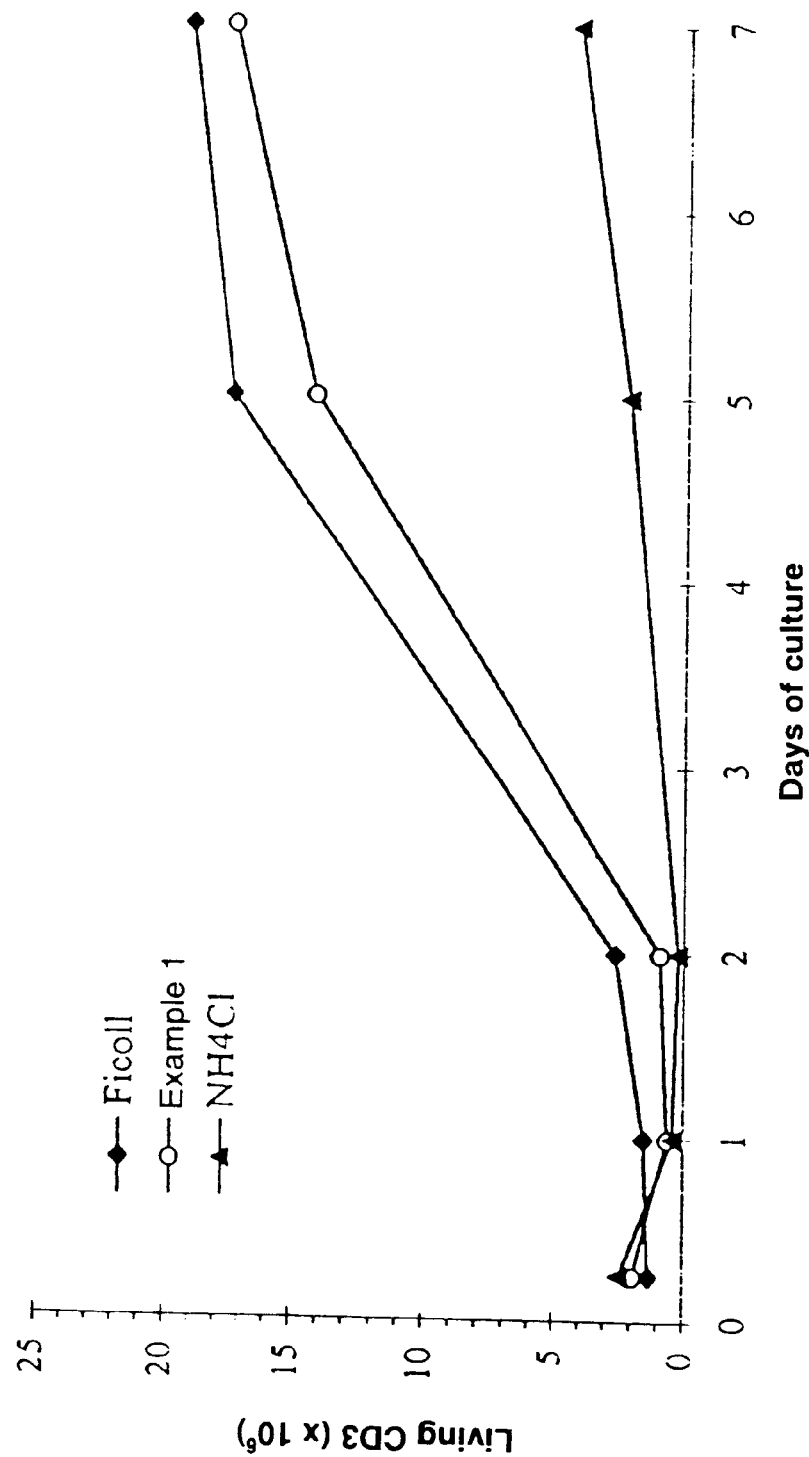

FIG. 2 represents the demonstration of cell viability after lysis by expansion of the T cells in a culture medium containing interleukin-2 and phytohaemagglutinin. The number of days of culture is represented on the abscissa and the number of living CD3 cells is indicated on the ordinate (in $10^6$ cells). The triangles, circles and squares represent respectively the results obtained with $NH_4Cl$, example 1 and Ficoll.

DETAILED DESCRIPTION OF THE INVENTION

The examples below illustrate the present invention.
Reference Preparation

A lysis reagent based on $NH_4Cl$ (ref. Ortho Diagnostics) was used.

EXAMPLE 1

Preparation of a Lysis Reagent

A lysis reagent corresponding to the following formula was prepared:

0.15M pyrrolidine—HCl 0.04M boric acid 0.005M HEPES 0.0001M EDTA

EXAMPLE 2

Preparation of a Lysis Reagent

A lysis reagent corresponding to the following formula was prepared:

0.15M pyrrolidine—HCl 0.04M boric acid 0.005M HEPES 0.0001M EDTA 0.1M formaldehyde pH 7.0

EXAMPLE 3

Preparation of a Lysis Reagent

A lysis reagent corresponding to the following formula was prepared:

0.15M piperidine—HCl 0.04M boric acid 0.005M HEPES 0.0001M EDTA pH: 7.0

EXAMPLE 4

Preparation of a Lysis Reagent

A lysis reagent corresponding to the following formula was prepared:

0.15M piperidine—HCl 0.04M boric acid 0.005M HEPES 0.0001M EDTA 0.1M formaldehyde.

Pharmacological Study

Experiment 1: Demonstration of the Lysis of Erythrocytes

Starting from blood with EDTA, two hours after sampling, samples of 100 μl were incubated for 15 minutes in the presence of 20 μl of monocyte markers (CD14-phycoerythrin) and leucocyte markers (CD45-FITC), sold by IMMUNOTECH under the reference IM 1201. The samples were then mixed with different lysis preparations, notably those described above, at different temperatures, subjected to lysis for 10 minutes at ambient temperature, then a part of the samples were taken up in phosphate buffer (PBS) after centrifugation (5 min, 300 g). The samples are stored at 4° C.

The samples were analysed on a FACSCAN cytometer (BECTON & DICKINSON) immediately or after having been washed with 3 ml of phosphate buffer and thereafter at 24 hour intervals, during storage.

FIGS. 1a–1d show the scattergrams of the lysed blood preparations analysed using the Simulset program (BECTON & DICKINSON). The percentages of lymphocytes, monocytes and granulocytes in the leucocyte formula were estimated on the basis of the diffusion diagram at large and small angles and CD45/CD14 fluorescence.

As a control, blood labelled with CD45-phycoerythrin (0.1 ml of blood per 0.02 ml of CD45-phycoerythrin, diluted 500 times in PBS without lysis) was analysed by cytometry by applying a threshold in the fluorescence channel FL2 (corresponding to 400 volts). The scattergrams of the leucocyte events are shown in FIG. 1A.

By comparing the control without lysis with the performance of the lysis reagent of example 1, example 2 and ammonium chloride (FIG. 1a, lines A, B, C and D), the morphology of the well preserved monocytes and lymphocytes may be seen, and a slight modification of the location of the polynuclear cells to the right, particularly in the case of $NH_4Cl$.

During storage, a shift in the polynuclear cells to the right as a function of time is also observed, indicating that this shift is associated with a partial deterioration of the polynuclear cells. During the storage of these samples, a shift of part of the lymphocytes and monocytes in the region of the debris is also observed, an effect which apparently does not depend on lysis because is it also observed in the control series (FIG. 1A).

The same phenomena are observed in the storage series after lysis and without washing of the method using the preparation of example 1 and example 2 (FIG. 1b, line H, FIG. 1c, line I).

This indicates that cell preservation in the reagents of examples 1 and 2 is no different to preservation in PBS. On the other hand, storage in $NH_4Cl$ (FIG. 1c, line J) shows a rapid degradation of the material.

Very good preservation was obtained with the reagents of examples 1 and 2 in the presence of formaldehyde after washing in PBS (FIG. 1b, lines E, F) or without washing (FIG. 1c, lines K, L).

In spite of the fact that $NH_4Cl$ and formaldehyde are incompatible, an attempt was made to create a mixture by replacing the $NH_4Cl$ used by formaldehyde according to the reaction described above. After lysis and washing, a shift of the polynuclear cells to the right was observed and the lymphocytes are rapidly destroyed and found with the debris (FIG. 1b, line G). Apparently, a little formaldehyde remains in the mixture because degradation in the product without washing (FIG. 1d, line M) is lower than with NH₄Cl without formaldehyde (FIG. 1c, line J).

Without washing, the reaction product of NH₄Cl and formaldehyde is apparently toxic for the cells because, in lysis with washing, considerable degradation with displacement of the granulocytes to the left and to the bottom occurred during storage (FIG. 1c, line J).

Experiment 2: Demonstration of the Cell Viability after Lysis

An estimate of cell viability was obtained by culture, in the presence of the RPMI 10% foetal calf serum medium and in the presence of phytohaemagglutinin 10 µg/ml and interleukin-2 (SIGMA, St-Louis, Mo., 20 unites/ml), of the leucocyte or lymphocyte populations after lysis or separation. A leucocyte population prepared by the method of example 1 was compared with a lymphocyte preparation prepared according to Boyum (Scandinavian Journal of Clinical and Laboratory Investigation 1967–1968, Suppl. 94–101.305.293) on Ficoll (Histopaque® SIGMA, St-Louis, Mo.) this latter being regarded as a reference method for lymphocyte preparation without loss of viability.

Also included is a preparation of leucocytes according to the method with NH₄Cl (ORTHO DIAGNOSTIC SYSTEMS Co., Raritan, N.J.).

In FIG. 2, the viability was demonstrated and estimated on the basis of the number in the culture of T cells (CD3+), non-necrotic or apoptotic according to labelling with annexin-5 (WO-A-95/27903). FIG. 2 shows the proliferation of T cells over time under the influence of phytohaemagglutinin and interleukin-2.

In conclusion:

The viability after lysis according to example 1 is substantially the same as that after Histopaque® separation, whilst the viability after lysis with ammonium chloride is greatly reduced.

What is claimed is:

1. In a lysis reagent composition capable of lysing erythrocytes and being used for the cytometric analysis of leucocytes, comprising a lysis agent and at least one other component, the improvement wherein said lysis agent is a nitrogenous heterocyclic compound and said composition has a pH between 4 and 9.

2. A composition according to claim 1 wherein said pH is between 5 and 8.

3. A composition according to claim 2 wherein said nitrogenous heterocyclic compound is monocyclic.

4. A composition according to claim 3 wherein said nitrogenous heterocyclic compound is saturated.

5. A composition according to claim 4 wherein said nitrogenous heterocyclic compound contains 3–8 carbon atoms.

6. A composition according to claim 2 wherein said nitrogenous heterocyclic compound is selected from the group consisting of pyrazolidine, imidazolidine and imidazoline, piperazine, morpholine, piperidine and pyrrolidine.

7. A composition according to claim 6 wherein said nitrogenous heterocyclic compound is present in said composition in a molar concentration of 0.01 to 0.2M.

8. A composition according to claim 7 wherein a said at least one other component comprises a compound containing chloride as its anion, said compound being present in an amount sufficient to confer said pH to said composition.

9. A composition according to claim 8 further comprising a counter-ion selected from the group consisting of hydrogen carbonate, another carbonate, and a borate.

10. A composition according to claim 1 further comprising a buffering agent.

11. A composition according to claim 10 further comprising an anticoagulant.

12. A composition according to claim 11 further comprising an aliphatic aldehyde.

13. A method for the lysis of erythrocytes comprising subjecting a sample of whole blood treated with an anticoagulant to a composition according to claim 6.

14. A method for the lysis of erythrocytes comprising subjecting a sample of whole blood treated with an anticoagulant to a composition according to claim 10.

15. A method for the lysis of erythrocytes comprising subjecting a sample of whole blood treated with an anticoagulant to a composition according to claim 12.

16. A composition according to claim 1 consisting essentially of an aqueous mixture of about 0.15M pyrrolidine chloride, about 0.04M boric acids about 0.0001M EDTA and about 0.005M HEPES at a pH of about 7.0.

17. A composition according to claim 1 wherein said nitrogenous heterocyclic compound is monocyclic.

18. A composition according to claim 1 wherein said nitrogenous heterocyclic compound is saturated.

19. A composition according to claim 1 wherein said nitrogenous heterocyclic compound contains 3–8 carbon atoms.

20. A composition according to claim 1 wherein said nitrogenous heterocyclic compound is present in said composition in a molar concentration of 0.01 to 0.2M.

21. A composition according to claim 1 wherein said at least one other component comprises a compound containing chloride as its anion, said compound being present in an amount sufficient to confer said pH to said composition.

22. A composition according to claim 21 further comprising a counter-ion selected from the group consisting of hydrogen carbonate, another carbonate, and a borate.

23. A composition according to claim 1 further comprising a buffering agent.

24. A composition according to claim 1 further comprising an anticoagulant.

25. A composition according to claim 1 further comprising an aliphatic aldehyde.

26. A method for the lysis of erythrocytes comprising subjecting a sample of whole blood treated with an anticoagulant to a composition according to claim 1.

* * * * *